US012746067B2

(12) United States Patent
Blau et al.

(10) Patent No.: US 12,746,067 B2
(45) Date of Patent: Sep. 29, 2026

(54) ADAPTIVE POSITIONING TECHNOLOGY

(71) Applicant: Stryker European Operations Holdings LLC, Portage, MI (US)

(72) Inventors: Arno Blau, Balingen (DE); Bernd Simon, Kiel (DE); Lars Metz, Kiel (DE)

(73) Assignee: Stryker European Operations Holdings LLC, Portage, MI (US)

( * ) Notice: Subject to any disclaimer, the term of this patent is extended or adjusted under 35 U.S.C. 154(b) by 0 days.

(21) Appl. No.: 19/022,056

(22) Filed: Jan. 15, 2025

(65) Prior Publication Data

US 2025/0288356 A1 Sep. 18, 2025

Related U.S. Application Data

(63) Continuation of application No. 18/130,973, filed on Apr. 5, 2023, now Pat. No. 12,364,540, which is a (Continued)

(51) Int. Cl.
*A61B 34/10* (2016.01)
*A61B 6/12* (2006.01)
(Continued)

(52) U.S. Cl.
CPC ................ *A61B 34/10* (2016.02); *A61B 6/12* (2013.01); *A61B 6/505* (2013.01); (Continued)

(58) Field of Classification Search
CPC . A61B 34/10; A61B 2034/2065; A61B 34/25; A61B 2034/107; A61B 2034/252; (Continued)

(56) References Cited

U.S. PATENT DOCUMENTS 6,666,579 B2 12/2003 Jensen
6,856,827 B2 2/2005 Seeley et al.
(Continued)

FOREIGN PATENT DOCUMENTS

DE 102009049819 A1 5/2011
EP 2801320 A1 11/2014
WO WO-2014048447 A1 * 4/2014 ......... A61B 17/1703

OTHER PUBLICATIONS

International Search Report for PCT/US2016/061288 dated Jan. 23, 2017, 2 pages.

(Continued)

*Primary Examiner* — Chao Sheng
(74) *Attorney, Agent, or Firm* — Lerner David LLP

(57) ABSTRACT

A method of treating a bone fracture includes taking a first 2D image of an implant and a reference body with an imaging device; creating a 3D orientation of the reference body and the implant based on the 2D image; determining an actual axis of delivery of a bone screw through an opening extending through the implant; determining an optimal axis of delivery of the bone screw through the opening such that the optimal axis of delivery guides the bone screw toward a medically optimal location; and moving the implant such that the optimal axis of delivery and the actual axis of delivery coincide.

16 Claims, 15 Drawing Sheets

Related U.S. Application Data continuation of application No. 15/774,053, filed as application No. PCT/US2016/061288 on Nov. 10, 2016, now Pat. No. 11,642,170.

(60) Provisional application No. 62/254,940, filed on Nov. 13, 2015.

(51) Int. Cl.

| | |
|---|---|
| ***A61B 6/50*** | (2024.01) |
| ***A61B 17/17*** | (2006.01) |
| ***A61B 34/00*** | (2016.01) |
| ***A61B 90/00*** | (2016.01) |
| ***G16H 20/40*** | (2018.01) |
| *A61B 17/00* | (2006.01) |
| *A61B 17/56* | (2006.01) |
| *A61B 17/74* | (2006.01) |
| *A61B 34/20* | (2016.01) |

(52) U.S. Cl.

CPC ...... *A61B 17/1717* (2013.01); *A61B 17/1725* (2013.01); *A61B 34/25* (2016.02); *A61B 90/37* (2016.02); *G16H 20/40* (2018.01); *A61B 2017/00725* (2013.01); *A61B 2017/564* (2013.01); *A61B 17/744* (2013.01); *A61B 2034/107* (2016.02); *A61B 2034/2065* (2016.02); *A61B 2034/252* (2016.02); *A61B 2034/254* (2016.02); *A61B 2034/256* (2016.02); *A61B 2090/363* (2016.02); *A61B 2090/376* (2016.02); *A61B 2090/3764* (2016.02); *A61B 2090/3966* (2016.02)

(58) Field of Classification Search

CPC ........ A61B 2034/254; A61B 2034/256; A61B 90/37; A61B 2090/363; A61B 2090/376; A61B 2090/3764; A61B 2090/3966; A61B 6/12; A61B 6/505; A61B 17/1717; A61B 17/1725; A61B 17/744; A61B 2017/00725; A61B 2017/564; G16H 20/40

See application file for complete search history.

(56) References Cited

U.S. PATENT DOCUMENTS

| | | | | |
|---|---|---|---|---|
| 7,065,393 | B2 | 6/2006 | Sati et al. | |
| 8,685,034 | B2 | 4/2014 | Giersch et al. | |
| 9,044,190 | B2 | 6/2015 | Rubner et al. | |
| 2002/0122536 | A1 | 9/2002 | Kerrien et al. | |
| 2006/0098851 | A1 | 5/2006 | Shoham et al. | |
| 2007/0274584 | A1* | 11/2007 | Leow | G03B 42/02 382/132 |
| 2008/0262345 | A1* | 10/2008 | Fichtinger | A61B 6/504 382/128 |
| 2009/0209851 | A1 | 8/2009 | Blau | |
| 2010/0041985 | A1 | 2/2010 | Simon et al. | |
| 2014/0214045 | A1 | 7/2014 | Felder et al. | |
| 2014/0275981 | A1* | 9/2014 | Selover | A61B 5/061 600/424 |
| 2014/0357985 | A1 | 12/2014 | Cardelino et al. | |
| 2015/0265361 | A1 | 9/2015 | Blau et al. | |
| 2015/0332465 | A1 | 11/2015 | Schmidt et al. | |

OTHER PUBLICATIONS

Extended European Search Report including Written Opinion for Application No. EP16864983.8 dated Jun. 14, 2019, pp. 1-11.

* cited by examiner

ADAPTIVE POSITIONING TECHNOLOGY

CROSS-REFERENCE TO RELATED APPLICATIONS

This application is a continuation of U.S. application Ser. No. 18/130,973, filed on Apr. 5, 2023, which is a divisional of U.S. application Ser. No. 15/774,053, filed on May 7, 2018, which is a national phase entry under 35 U.S.C. § 371 of International Application No. PCT/US2016/061288, filed Nov. 10, 2016, which claims the benefit of the filing date of U.S. Provisional Patent Application No. 62/254,940 filed Nov. 13, 2015, the disclosures of which are hereby incorporated herein by reference.

BACKGROUND OF THE INVENTION

The invention relates to the field of computer based assistance of surgery. In particular, the invention relates to a method of automatic image processing including an interpretation of the content of for example an x-ray image. The method may be implemented as a computer program executable on a processing unit of a suitable device.

In every surgery where intraoperative imaging is used it is a challenge to accurately perform the necessary steps of a procedure of treating a bone fracture. Usually, almost each step requires an iterative process based on several X-ray images. A significant radiation exposure is thus produced. The amount of radiation may be highly dependent on the know-how and skill of the physician.

Some systems may provide virtual information about current position of an implant related to a bone. Also it may be possible to provide information on how to adjust the current implant or instrument position to optimise the current procedural steps. However, the availability of this information is highly dependent on the visibility of necessary structures in the image, like a reference body, a certain anatomical structure, an aiming device, a drilling sleeve or the like.

U.S. Pat. No. 6,856,827 B2 describes a system for surgical imaging and display of tissue structures of a patient, including a display and an image processor for displaying such image in coordination with a tool image to facilitate manipulation of the tool during the surgical procedure. The system is configured for use with a fluoroscope such that at least one image in the display is derived from the fluoroscope at the time of surgery. The fixture is affixed to an imaging side of the fluoroscope for providing patterns of an array of markers that are imaged in each fluoroscope image. A tracking assembly having a plurality of tracking elements is operative to determine positions of that fixture and the patient. One of the tracking elements is secured against motion with respect to the fixture so that determining a position of the tracking clement determines the position of all the markers in a single measurement.

BRIEF SUMMARY OF THE INVENTION

It may be seen as one aspect of the invention to provide a device for more effeciently assisting in performing a surgical procedure. It would be highly benefitial to reduce the amount of radiation to which a patient is exposed, and to have a more effectient way to directly evaluate the content of images or to move to a next step of a workflow.

In accordance with the invention, a computer based assistant is provided which is capable of monitoring the course of a treatment procedure. That assistant is capable of evaluating a current treatment step based on a single x-ray projection image, and is capable of suggesting a next step or a series of next steps. In a case in which a treatment process is performed in a more or less optimal way, the computer based assistant will lead straight forward through the procedure. However, should the treatment process be performed incorrectly, i.e. with a risk of a poor medical result, the computer based assistant is able to suggest at least one additional step, e.g. a correction step, so as to improve the result of the treatment procedure.

In particular, the computer based assistant may be capable of suggesting one or more steps, which steps may be performed without requiring the generation of a new x-ray image. By way of this, the overall amount of x-ray radiation can be reduced to which the patient is exposed.

The mentioned objects are solved by the subject-matter of each of the independent claims. Further embodiments are described in the respective dependent claims.

First of all, a computer program element is provided executable by a processing unit for processing a 2D projection image generated during a procedure of fracture treatment of a bone. The computer program element may comprise sets of instructions for detecting a reference body as well as an instrument and/or an implant and/or an anatomical structure in the 2D projection image. For example, grayscale values of pixels may be identified and compared with adjacent grayscale values so as to detect contour lines or points in an x-ray image.

The reference body may be directly attached to an anatomical structure, e.g. may be in contact with an outer surface of a body part of interest. The reference body may also be indirectly coupled to an anatomical structure, for example via a handling tool for inserting an implant. On the other hand, the reference body may be at least a part of an implant. In other words, an implant which is adapted to be fixed at or in a bone may comprise elements which can be identified in an image of the bone or at least a section of the bone so that geometrical aspects may be determined based on the identified elements. For example, the elements may define points so that two elements may define a line or an axis, or the elements may define a contour so that a center axis may be determined.

According to an embodiment, the reference body may be integrated into an aiming device for supporting an insertion of a locking screw through a bore in a leading end of a bone nail, wherein the aiming device may be adapted to be coupled to the handling tool for inserting the bone nail. Therefore, the aiming device may be adapted to be coupled to a trailing end of the bone nail and may extend outside the body of a patient as far as the bone nail extends inside the bone so that at least a portion of the aiming device can be visible in an image of the section of the bone including the leading end of the bone nail. Such an aiming device is described and shown in U.S. Pat. No. 8,685,034, the disclosure of which is incorporated herein by reference.

As used herein, the term "anatomical structure" refers to anything at a bone and in particular to a geometrical aspect of a bone, i.e. a point, a line, an arc, a center point, an axis, a cylinder surface, a ball surface, or the like. For example, a geometrical aspect of a femur may be the outer surface of the femur head, an axis defined by the neck between shaft and femur head, a longitudinal axis of the femur shaft, a most distal point on the bone surface, a line defined by the center points of the condyles, or a line defined by the most posterior points at the condyles. It will be understood that the other bones provide other and/or comparable suitable geometrical aspects.

The computer program element may further comprise sets of instructions for identifying a current state of each of the detected elements. Here, "current state" means first of all a position and orientation of the detected element. As will be described in detail below, the position and orientation of the reference body can be determined due to the specific distribution of fiducial markers forming the reference body. With respect to an instrument, like a gauge or a drill or a K-wire, the position may be detected in relation to the reference body and/or to an anatomical structure. A "current state" of an instrument may also include a deformation or bending of the instrument. Furthermore, a "current state" may indicate the appearance of the instrument and/or of an implant or sub-implant in the 2D projection image.

Based on the identified state of the detected elements, a state of progress of the procedure of fracture treatment may be determined. For example, the processing unit may execute sets of instructions so as to compare information provided by a database with the results of the previously performed steps, with the database including data defining each step out of a sequence of steps necessary to perform a fracture treatment procedure. For example, the steps may be defined in the database by the respective state of the elements which elements are involved in the particular step, so that information extracted from the 2-D projection image can be compared with information received from the database.

The step following the identified step out of the sequence of steps in the database may be used by the processing unit to provide information which step should be performed next. Such information can, for example, be shown on a monitor as information assisting in the fracture treatment.

When comparing the database information with the identified state of the detected elements, the processing unit, when executing sets of instructions of the computer program element, may determine a deviation of the current state of the element from a target state of the element in which the element should be in the determined state of progress. Further, a degree of deviation may be determined, and the degree of deviation may be compared with a predetermined threshold value. In a case in which the determined deviation exceeds the threshold value, at least a warning may be provided, but also a suggestion to undo a step.

The determined deviation may also be translated by the processing unit into an adjustment movement of an extra-corporeal handling device, i.e. a handling device being outside of a body of a patient. For example, an adjustment movement may be a translational or a rotational movement of a handle of an instrument in a specific direction so as to shift an implant in a longitudinal direction thereof or to tilt or rotate the implant. The kind and degree of the adjustment movement may be optically or acoustically provided.

According to another embodiment, the computer program element may further comprise sets of instructions for determining a 3D orientation of the reference body relative to a projection direction and/or to a projection plane of the 2D projection image. A projection direction of the imaging system may be provided by sensors arranged at for example the C-arm driving unit.

Based on the determined position and orientation of the reference body, a space may be determined in the anatomical structure with a pre-determined relation to the reference body, with the space being adapted to accommodating an implant. It is to be noted that the implant may not yet be implanted, but is intended to be implanted into the anatomical structure, so that no projection of the implant is visible in the 2D projection image. Additionally, information may be received related to a space in the anatomical structure having an optimal spatial position and orientation relative to the anatomical structure.

According to an embodiment, a deviation between the space with the pre-determined relation to the reference body and the space with the optimal spatial position and orientation in the anatomical structure is determined. The determined deviation may be optically or acoustically provided. A visualization of the pre-determined space may be provided, for example in form of outlines of the space projected onto the 2D projection image.

According to another embodiment, the computer program element may further comprise sets of instructions for detecting and identifying a bone fracture in the 2D projection image. Based on a detected and identified bone fracture, a processing unit may automatically select a sequence of steps from the database related to a treatment of the identified fracture.

The computer program element may preferably be loaded into a work memory of a data processor. The data processor or processing unit is thus equipped to carry out the method. Further, the invention relates to a computer-readable medium such as a CD-ROM at which the computer program element may be stored. However, the computer program element may also be presented over a network like the World Wide Web and can be downloaded into the working memory of the data processor from such a network.

According to another aspect, a device for assisting a physician in performing a surgical procedure is proposed, the device comprising a receiving unit for receiving a 2D projection image of an anatomical structure from a C-arm based imaging device, a processing unit, and a computer program element as described above, wherein the instructions of the computer program element are adapted to be executed by the processing unit of the device. The device may further comprise a reference body having a structure allowing a determination of a 3D orientation of the reference body based on a 2D projection image.

It is noted, that the processing unit may be realized by only one processor performing all the steps of the method, or by a group or plurality of processors, for example a system processor for processing the image data, a separate processor specialized on a determination of geometrical aspects, and a further processor for controlling a monitor for visualizing results.

According to another embodiment, the device may further comprise an input unit for receiving an input for interactively controlling the computer program clement and thus a workflow of the device. The input unit may be for example a computer keyboard, a computer mouse or a touch screen, so that the input unit may be adapted for manually identifying geometrical aspects of an anatomical structure like a bone in an image. Otherwise, the input unit may also be an electronic interface for receiving data sets representing a workflow of a procedure.

According to yet another embodiment, the device may further comprise a monitor for visualizing information.

It has to be noted that embodiments are described with reference to different subject-matters. In particular, some embodiments are described with reference to method type claims (computer program) whereas other embodiments are described with reference to apparatus type claims (system). However, a person skilled in the art will gather from the above and the following description that unless other notified in addition to any combination of features belonging to one type of subject-matter also any combination between features relating to different subject-matters is considered to be disclosed with this application. The aspects defined above and further aspects, features and advantages of the present invention can also be derived from the examples of the embodiments to be described hereinafter and are explained with reference to examples of embodiments also shown in the figures, but to which the invention is not limited.

Figure 1A:
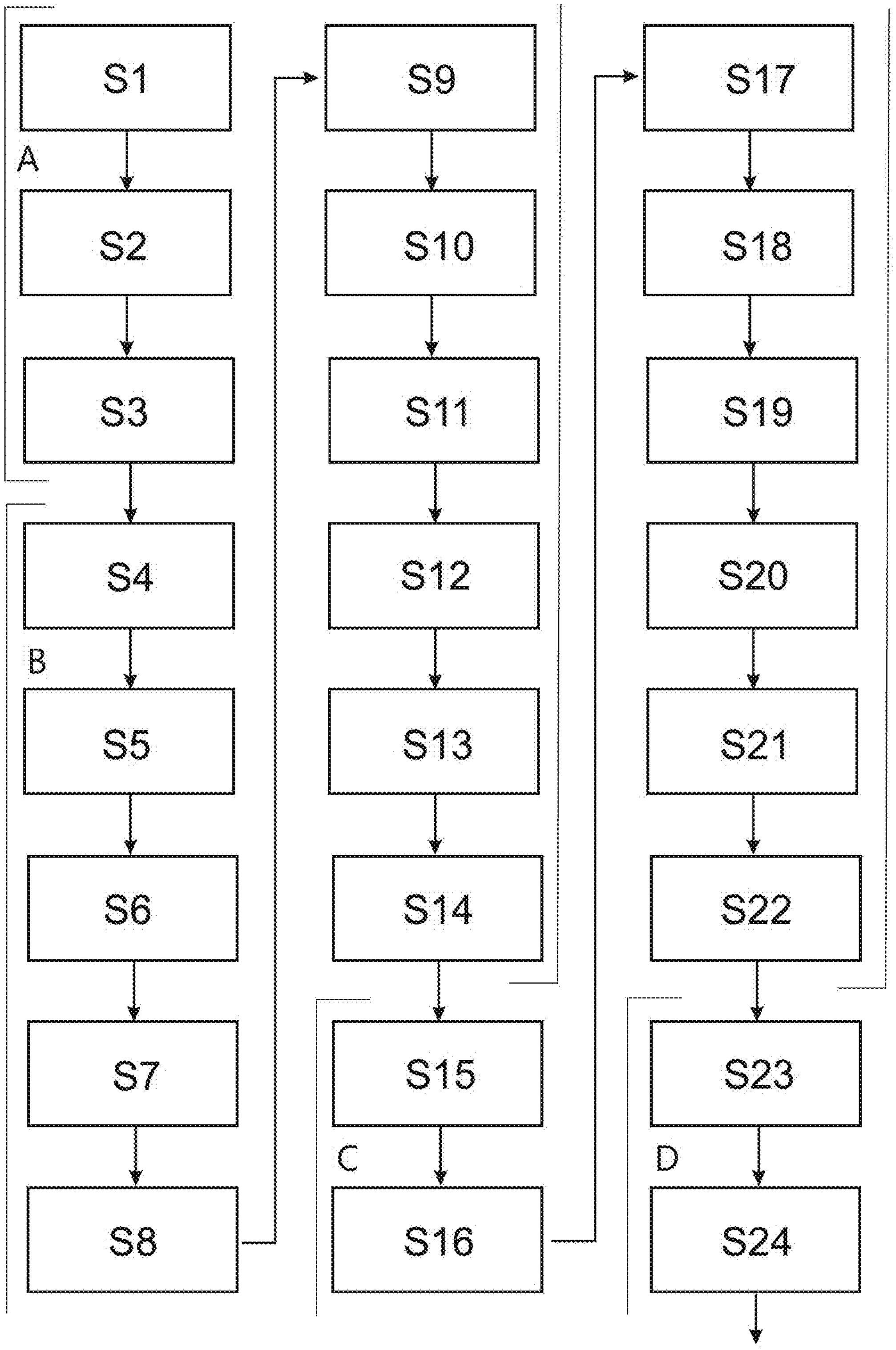
FIGS. 1*a* and 1*b* show a flow chart of steps of a method.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures.

DETAILED DESCRIPTION

Figure 1B:
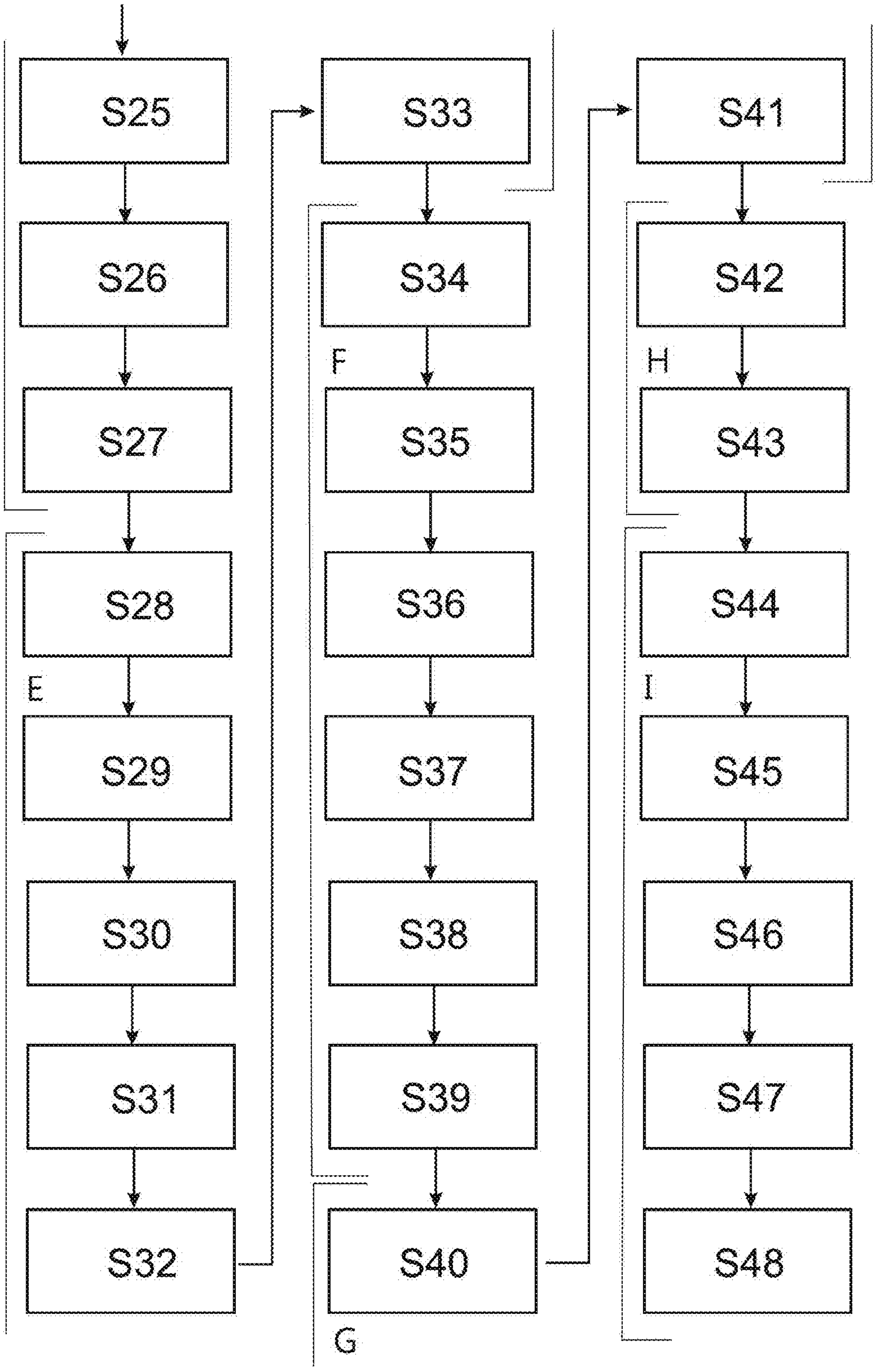

The flow-chart in FIGS. 1*a* and 1*b* (first page FIG. 1*a* and second page FIG. 1*b*) illustrates steps performed in accordance with embodiments. It will be understood that the steps described, may be major steps, wherein these major steps might be differentiated or divided into several sub-steps. Furthermore, there might be also sub-steps between the steps. Consequently, groups of steps may be related to a major aspect which may also be performed separately, i.e. independent from other steps or groups of steps. Examples of such groups of steps are indicated in FIGS. 1*a* and 1*b* by the brackets and reference signs A, B, C, D, . . . , I.

In the following, a method is described illustrating assistance in form of automatically generated information for a surgeon performing, as an example, an implantation of an intramedullary nail into a femur. It will be understood, that the principles described in this example may also be applied so as to assist a surgeon when fixing a fracture at other bones of a human body.

It is noted that some steps are described as being performed "if necessary". This is intended to indicate that those steps may be omitted. It is in particular noted that the computer program element may comprise sets of instructions to automatically recognize if a step is necessary or not, and to automatically proceed with the next actually necessary step.

The method starts at an instance in which the implant is already inserted into the fractured bone, but is not fixed by means of bone screws. The implant is connected in a predetermined way to an insertion instrument. A reference body is positioned in a predetermined relation to the implant, so that the reference body is visible in an x-ray image showing also the fractured bone as well as the inserted implant. Such an x-ray image may be generated by means of a typically used C-arm based x-ray device which is roughly positioned relative to the patient so as to image the femur head in an A/P direction, i.e. an anterior to posterior direction.

In step S1 of the method, a first image is received by a processing unit and may be shown on a monitor. In step S2, the processing unit detects points in the image, the points having a high contrast and being related to a reference body.

Figure 3:
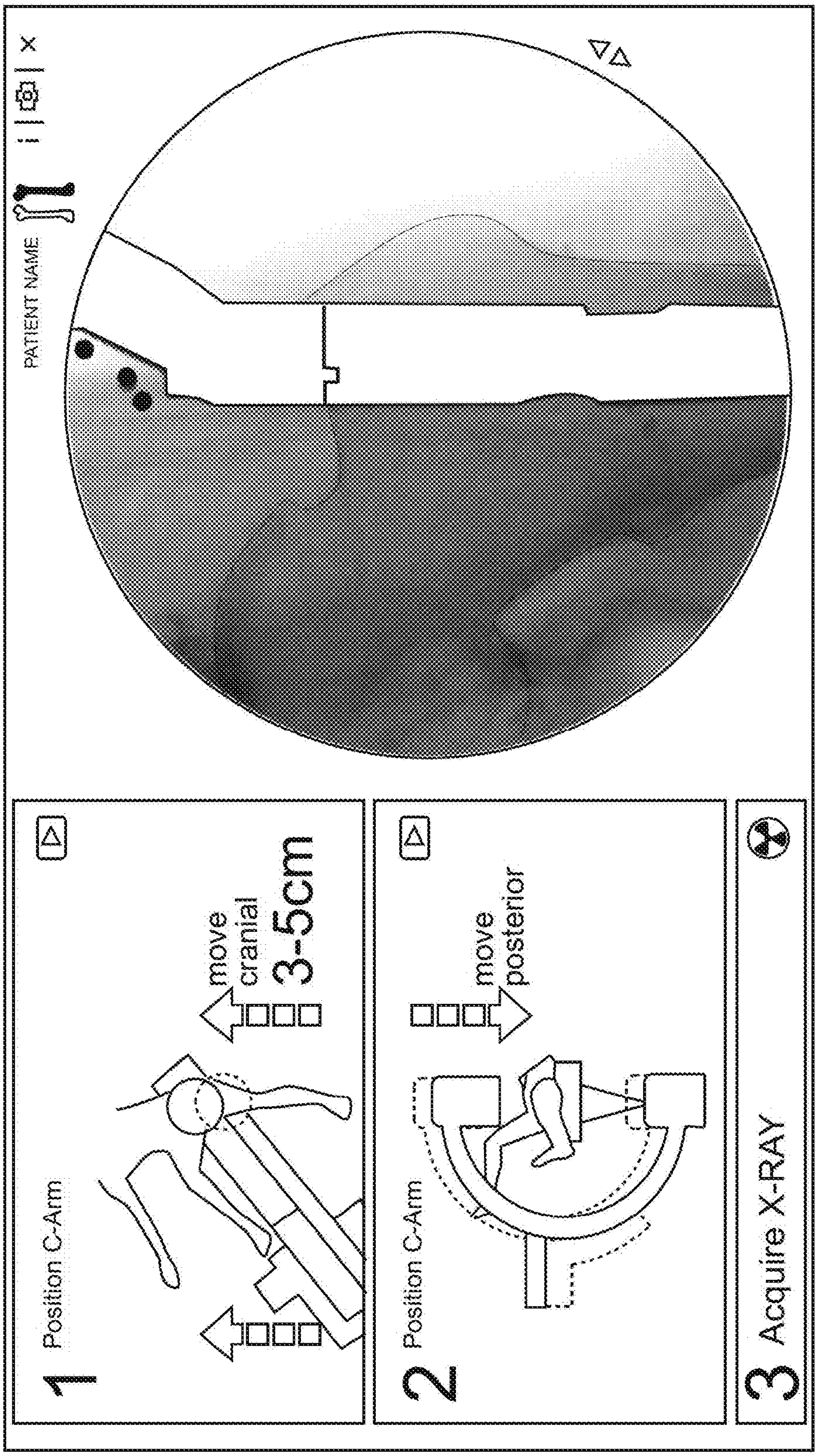
FIG. 3 is an example of a monitor visualization representing a first state of progress of the method.

In step S3, the processing unit determines as to whether enough points are detectable in the image so as to allow a determination of a three-dimensional orientation of the reference body relative to the imaging device. In the example shown in FIG. 3, the number of points of the reference body is not enough. In such a case, the processing unit calculates as to whether the imaging device should be shifted, taking into account for example the sizes and distances between the detected points of the reference body as well as information of absolute sizes and distances of fiducial markers forming the reference body, with the information being taken for example from a database. Based on the information taken from the (x-ray) image as well as the information taken from the database, the processing unit is capable of determining a shifting direction as well as a shifting length or distance for the imaging device relative to the patient's body so as to achieve images including enough detectable points of the reference body. In the example of a monitor image in FIG. 3, it is indicated on the left side of the monitor image that the imaging device should firstly be moved cranially by 3 to 5 cm and secondly be moved posterior. It is also indicated on the monitor that a new image should be generated after the new positioning of the imaging device. The sequence of steps S1 to S3 can be understood as a first aspect of the overall method, which aspect may only be performed if necessary, for example in a case as described.

Figure 4:
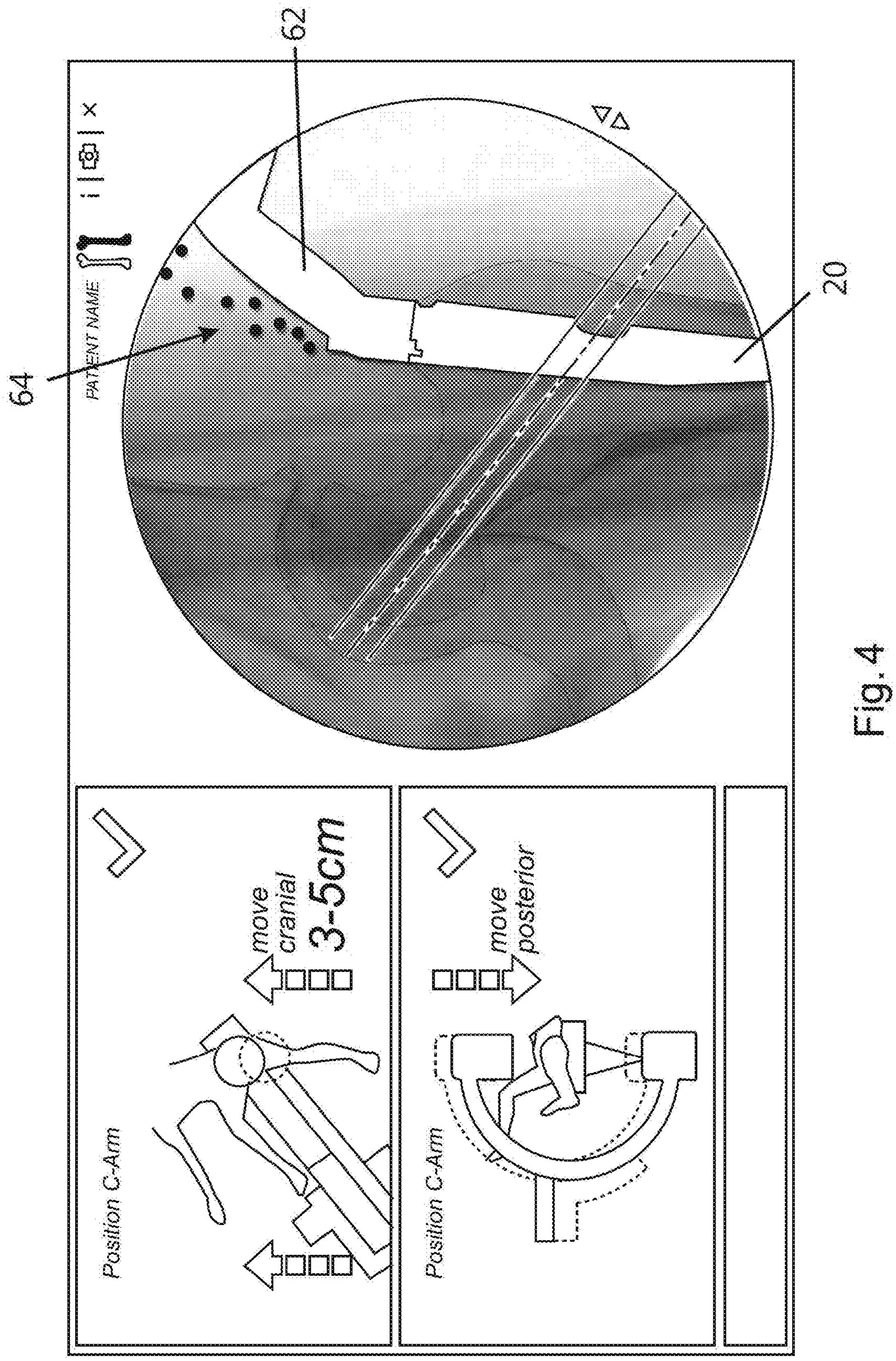
FIG. 4 is an example of a monitor visualization representing a second state of progress of the method.

In step S4, a new image is received by the processing unit of the system and may be shown on the monitor. In step S5, the processing unit detects points related to the reference body and determines in step S6 as to whether enough points are detectable as a basis to determine a three-dimensional orientation of the reference body in relation to the known position and orientation of the imaging device. If there are enough points detectable, the processing unit provides information, visible on the monitor, that this is the case (step S7). This can be visualised by a check mark as shown in the example of FIG. 4.

The reference body should be positioned so that the reference body will be imaged together with the anatomical structure of interest, as the reference body comprises a structure allowing a determination of the 3D orientation of the reference body based on a 2D projection image. The reference body will thus appear in the image of the anatomical structure. An appropriate position of the reference body is consequently beside or above, i.e. nearby the anatomical structure of interest. It is possible, but not necessary that the reference body is inside the anatomical structure.

In step S8, the actual three-dimensional orientation and position of the reference body in relation to the imaging device is determined based on a single two-dimensional projection image as generated and provided by the imaging device. In the following, the principles of such a determination are described.

Figure 5:
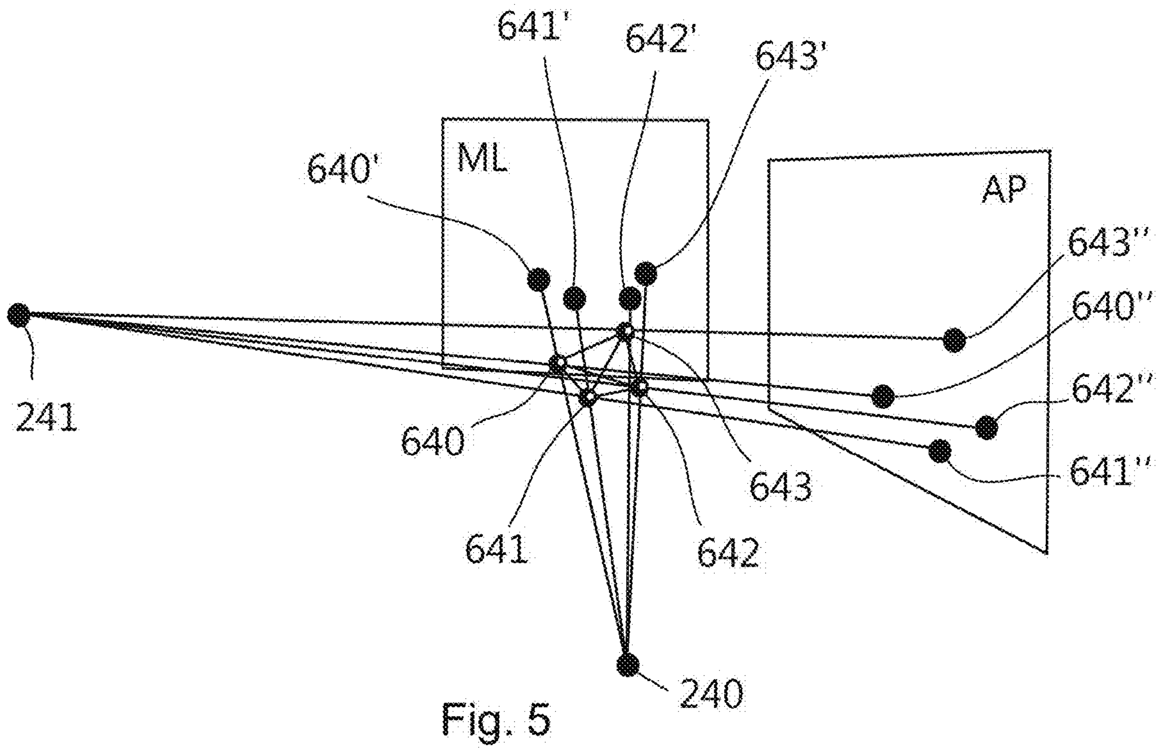
FIG. 5 is schematical visualization regarding a projection of a reference body.

FIG. 5 shows a reference body formed, in the example, by four spheres 640, 641, 642, 643 being arranged in space in a predetermined way. Further shown are lines representing x-ray beams emitted by an x-ray source 240, 241, respectively. Each line ends on one of the projection surfaces denoted as AP (anterior-posterior) or ML (medio-lateral). On the projection surface ML, the spheres of the reference body form a first pattern of projection points 640', 641', 642' and 643', and on the projection surface AP, the spheres form a second pattern of projection points 640", 641", 642" and 643". As can be easily seen, the first pattern on the surface ML differs from the second pattern on the surface AP. A skilled person will appreciate that it is possible to arrange spheres of a reference body in three-dimensional space such that a unique projection pattern will be achieved for each projection direction. Consequently, it is possible to determine the imaging direction, based on the detected projection pattern, and to determine the actual orientation of the reference body in space in relation to the imaging device. Furthermore, as the beams follow a fan angle, the spatial position, i.e. the distances of the references body to the x-ray source and the x-ray detector, respectively, can be calculated based on measured distances of the projection points. In fact, it is merely a matter of geometry to calculate the actual position and orientation of the reference body based on a single projection of the same.

Figure 6:
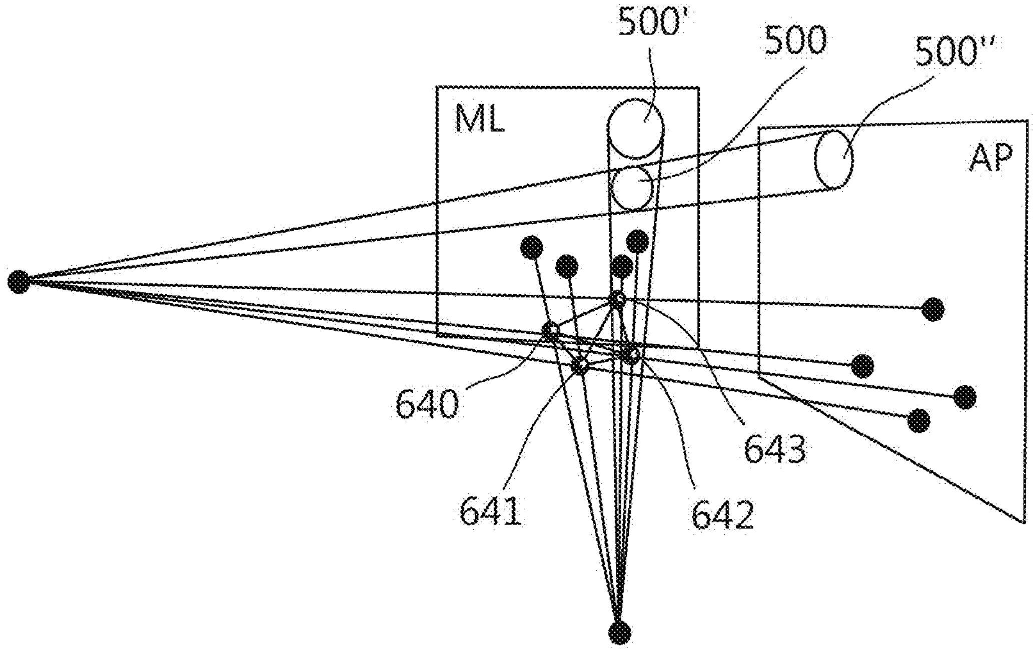
FIG. 6 is schematical visualization regarding a projection of a reference body together with an anatomical structure.

With the reference body as a "spatial anchor", it is also possible to determine an actual position and orientation of an anatomical structure based on a single x-ray image, as schematically illustrated in FIG. 6. Here, a projection of a head 500 of a femur, i.e. of a ball head is shown on each of the projection surfaces, wherein the relation of the projection 500' to the projections of the reference body on the surface ML differs from the relation of the projection 500" to the projections of the reference body on the surface AP. This illustrates that the projections of the reference body and the relation to the anatomical structures in the projection image are unique for each imaging direction. Consequently, the spatial position and orientation of the reference body can be determined and also the spatial position and orientation of the anatomical structure in the vicinity of the reference body, based on one x-ray image.

Figure 7:
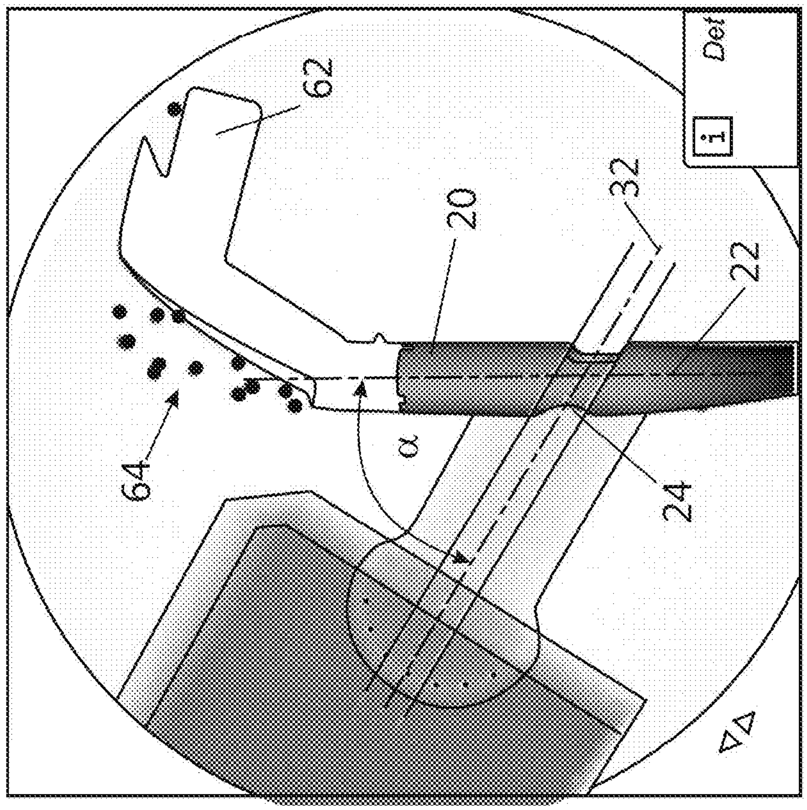
FIGS. 7 and 8 illustrate different appearance of one angle when being projected with different projecting directions.
Figure 8:
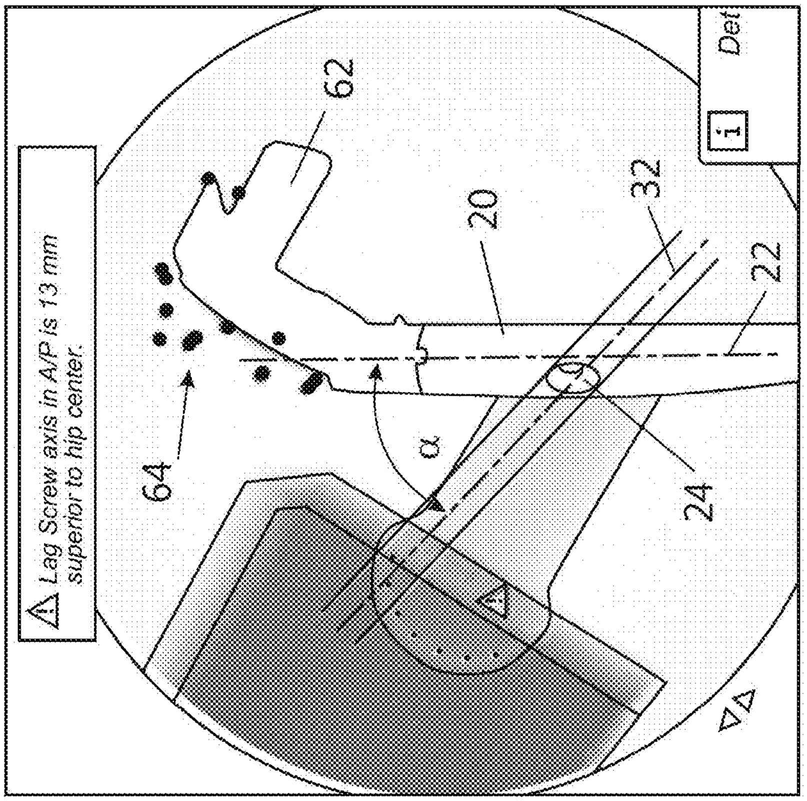

In step S9, the spatial position and orientation of the implant associated with the reference body is determined. Taking into account dimensions and structural features of the implant as provided for example by a database, this step includes also a determination of the position and orientation of for example a through hole through which a sub-implant, i.e. a fixation screw is to be inserted. Based on the determined structural aspects of the implant, a space or corridor for the sub-implant can be determined in step S10. This spatial space or corridor may then be projected onto the projection plane of the x-ray detector, so that the corridor having for example a centre axis as well as outer contour lines can be inserted into the current x-ray image as an overlay. Examples for such x-ray images including an indication of a space or corridor for a sub-implant are shown in FIGS. 7 and 8. In both examples, the actual through hole 24 in the implant 20 is inclined relative to a longitudinal axis 22 of the implant with an angle of 125°. However, as the implant 20 in FIG. 7 has another spatial orientation when compared with the implant in FIG. 8, i.e. the implant 20 in FIG. 8 has another rotational orientation, the inclination angle α (alpha) of the corridor axis 32 relative to the implant axis 22 appears to be different in the projections.

In step S11, an anatomical structure of interest is identified in the x-ray image. As shown in FIGS. 7 and 8, a femur head may be such an anatomical structure of interest, which femur head may be defined by its outer surface 12 as well as its centre point 14. As will be appreciated by a skilled person, the higher density of for example a joint surface of a bone will result in a higher absorption of x-ray radiation which is typically visualized in the resulting image with a darker grayscale value. Such darker grayscale value can be identified so as to detect a contour line of the outer surface 12. The centre point 14 is geometrically defined by the curved contour line.

When determining the actual spatial orientation and position of the femur head, information related to the reference body and the knowledge about the actual relative positioning of the reference body in the vicinity of the anatomical structure can be taken into account. For example, pixel values may be assessed in particular in an area in which the femur head can be expected due to a distance to the reference body.

This information allows for a determination of a deviation of the corridor axis 32 from for example the centre point 14 of the femur head (step S12). Such a deviation is indicated in the example shown in FIG. 9.

Figure 9:
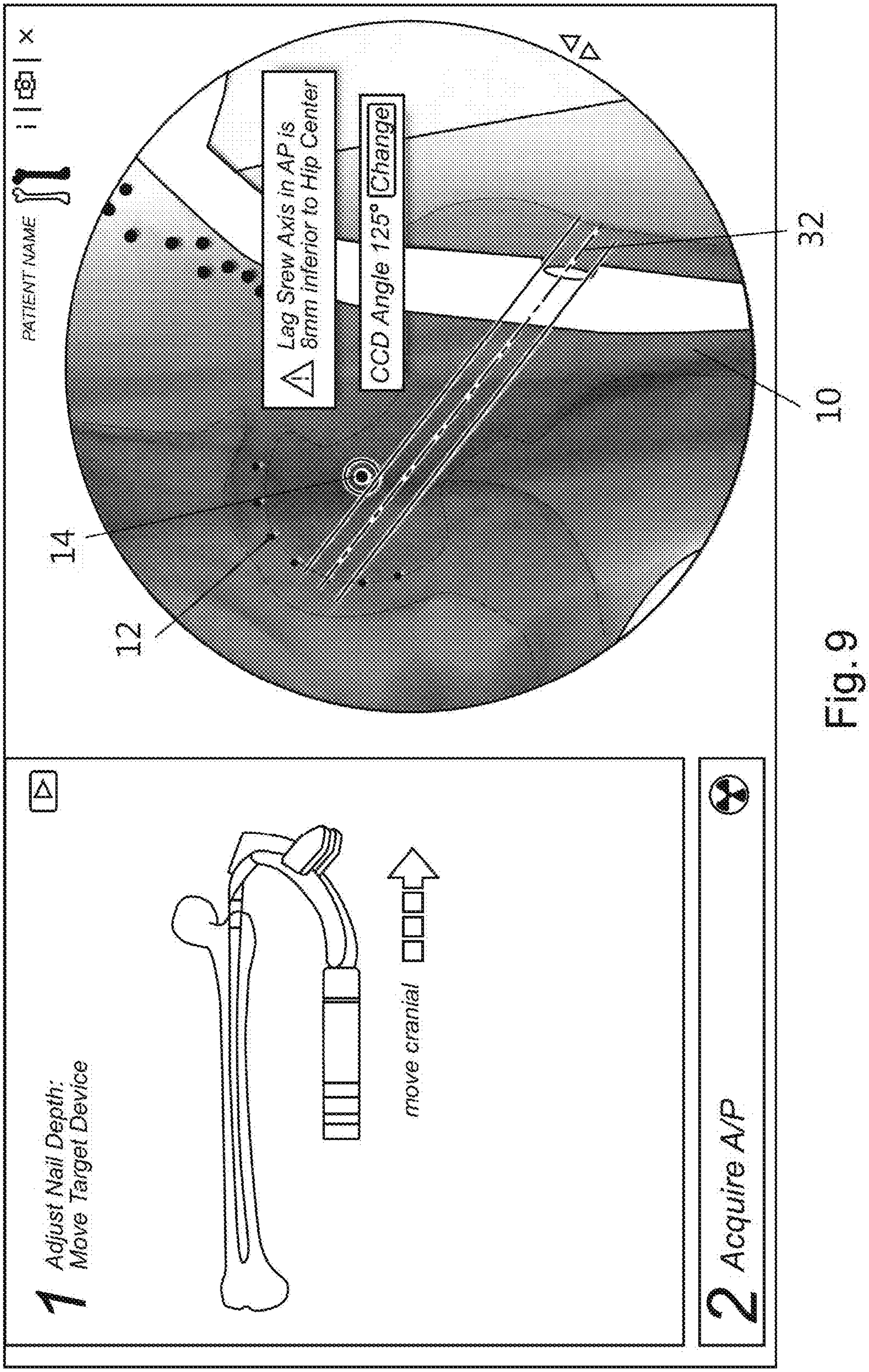
FIG. 9 is an example of a monitor visualization representing a third state of progress of the method.

In step S13, the determined deviation may be translated into an instruction to move the implant for example cranially, wherein such an instruction can be visualized on the left side of the monitor as in the example of FIG. 9. In a following x-ray image, the positioning of the implant within the femur can be verified, at least for the anterior-posterior (AP) projection direction.

Figure 10:
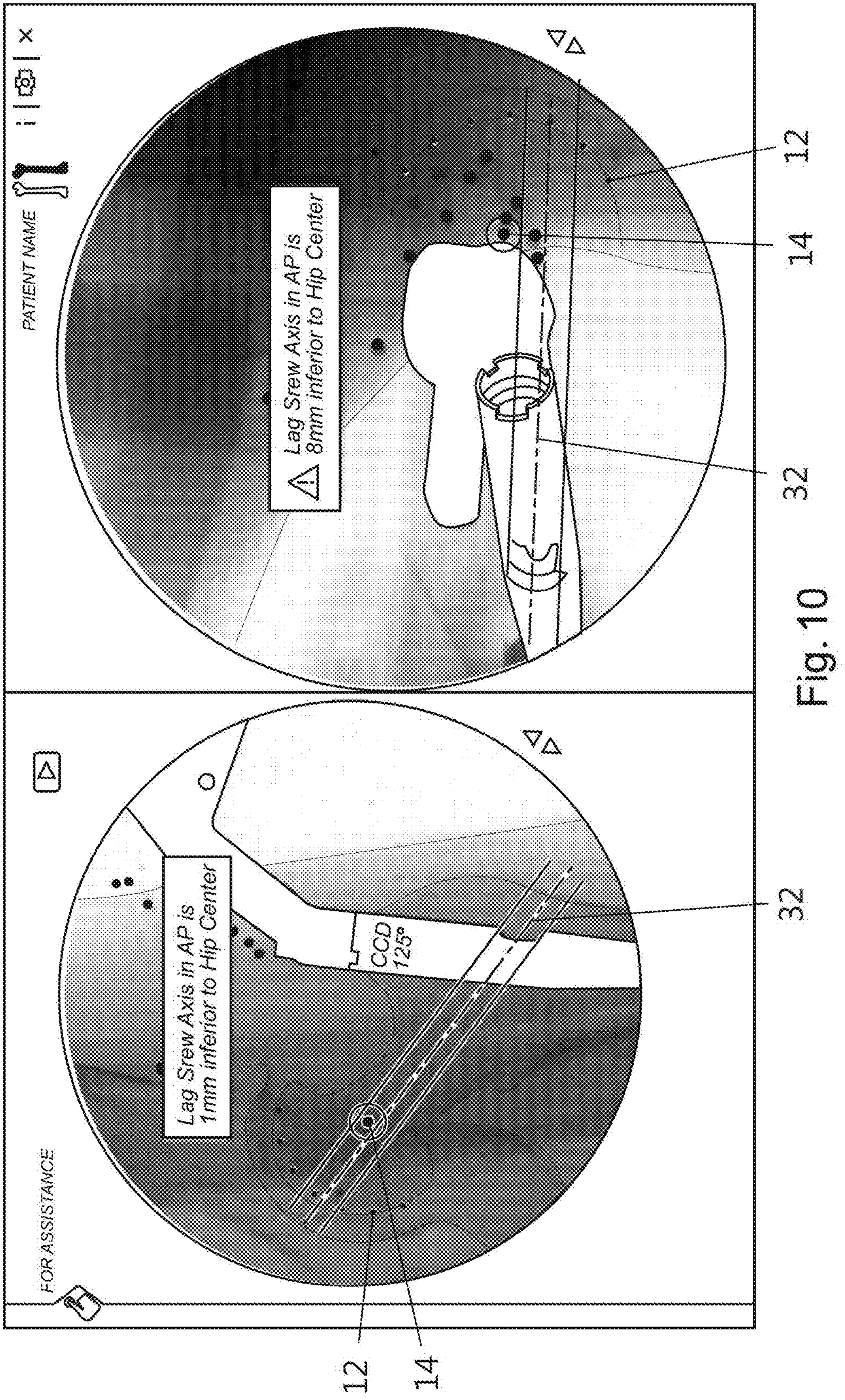
FIG. 10 is an example of a monitor visualization representing a fourth state of progress of the method.

In step S14, a similar procedure starts with a first image generated in a medio-lateral (ML) imaging direction. As shown in the example of FIG. 10, the last AP x-ray image may be shown side by side with the first ML x-ray image on the monitor, both images including an indication of an insertion corridor with axis 32 for a sub-implant, i.e. for a locking screw, as well as in indication of the outlines 12 and of the centre point 14 of the femur head.

The sequence of steps S4 to S14 may be considered as an aspect or as an embodiment B (cf. FIG. 1*a*).

In the following steps, the same principles as described above are applied. Points related to the reference body may be detected in the x-ray image (step S15) and, if necessary, instructions are provided for a correction of the imaging parameters (step S16). Based on a sufficient number of points of the reference body, the spatial orientation and position of the same is determined (step S17) as well as the position and orientation of the implant associated with the reference body (step S18). Also here, a deviation between a corridor for a sub-implant and the optimal position and orientation of the sub-implant to be implanted can be determined (step S19) and visualized as an overlay in the x-ray image (step S20), with the spatial orientation of the corridor being projected onto the image plane.

Figure 11:
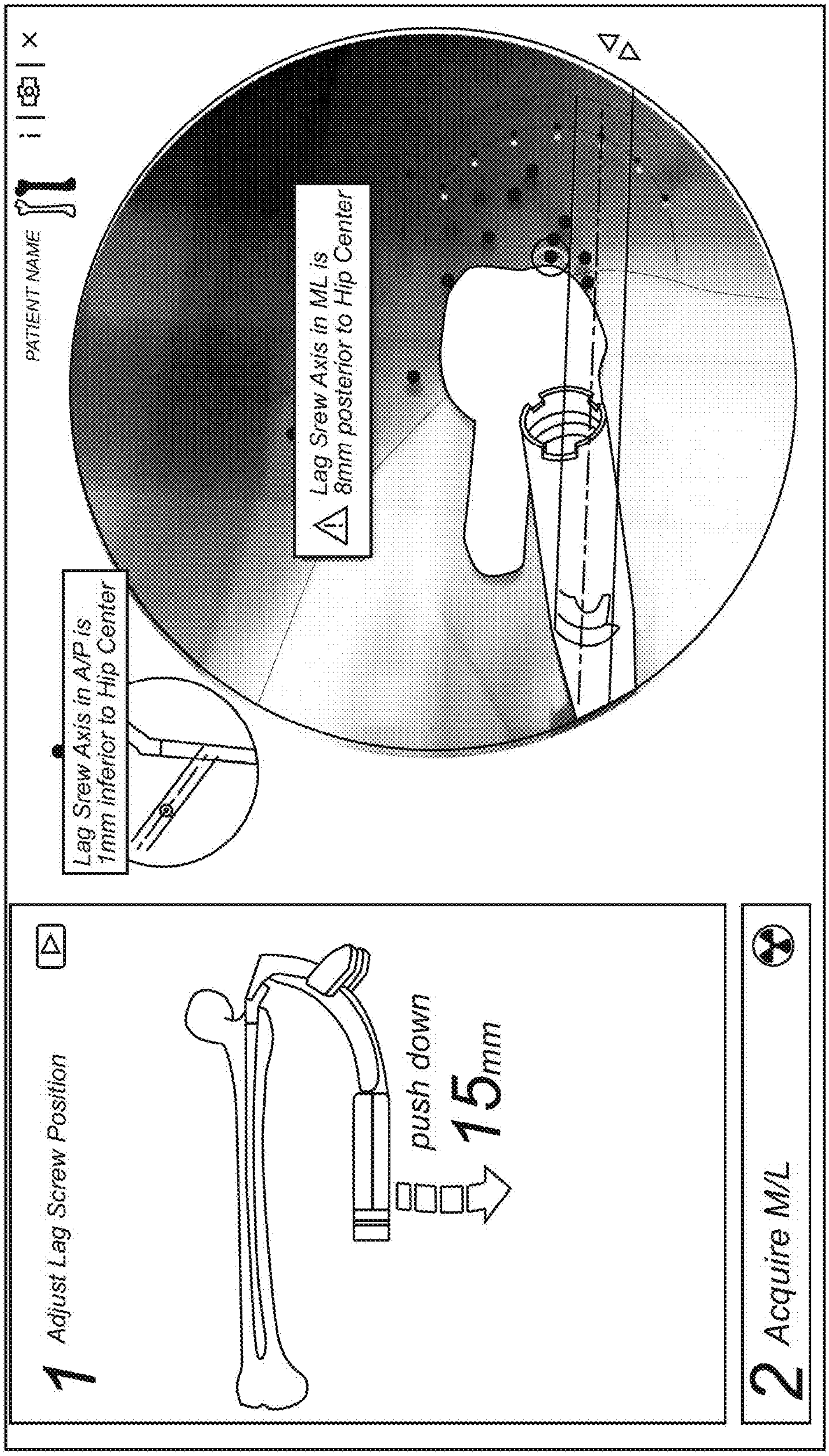
FIG. 11 is an example of a monitor visualization representing a fifth state of progress of the method.

As shown on the left side in the example of FIG. 11, the detected and calculated deviation of the sub-implant corridor is shown, the corridor indicating a position and orientation of a sub-implant which would be arranged in this corridor if it would be implanted or inserted through the through hole of the already implanted main-implant. The detected position and orientation of the already implanted main-implant can be determined as being not acceptable when taking into account a sub-implant corridor which would be optimal from a medical point of view. The detected position and orientation of the main-implant may be translated into an instruction as to how that implant has to be moved to shift the sub-implant corridor to the position and orientation of the optimal sub-implant corridor (step S21). In the example shown in FIG. 11 the determined deviation of 8 mm posterior to optimal is translated in an instruction to push the handle of the inserting device for the already implanted implant down by 15 mm, which instruction is shown on the monitor (step S22).

It will be understood that the sequence of steps S15 to S22 are based on the same principles as the sequence of steps S4 to S14 as described above. The sequence of steps for achieving an accurate ML positioning of the implant (before fixation of the same) is indicated in FIG. 1*a* by the reference sign C.

With a new image, the corrected position and orientation of the sub-implant space or corridor can be controlled and also visualised on the monitor, and further a sequence of steps can be shown which should be performed before a further x-ray image has to be generated. A physician may for example be instructed (i) to insert a sleeve assembly so as to allow drilling up to and into the femur head, and/or (ii) to insert a K-wire sleeve so as to support an insertion of a K-wire, and/or (iii) to determine a length of a screw which screw would fit into the femur head. Together with such instructions, both images of the AP imaging direction and the ML imaging direction can be shown on the monitor, wherein the size of the visualized AP image may differ from the size of the visualized ML images. For example, the ML image may be shown in full size whereas the AP image may be shown rather small for a general view without details (see the example of FIG. 11).

Figure 12:
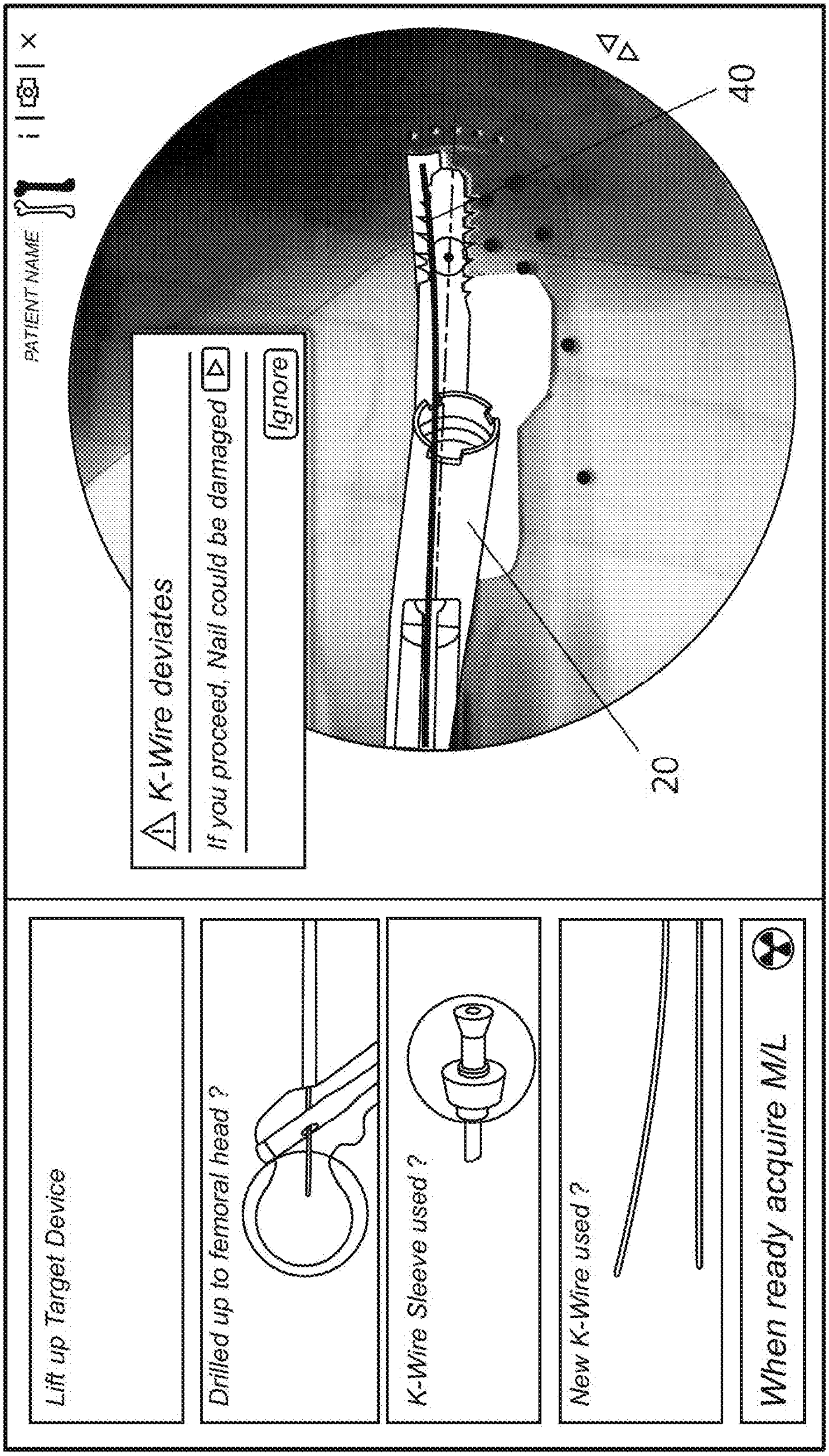
FIG. 12 is an example of a monitor visualization representing a sixth state of progress of the method.

Another aspect is described at the example of an insertion of a K-wire. In step S23, an image is received showing a situation in which a K-wire 40 is already inserted through the through hole of the already implanted implant and into the femur head. However, it may occur that the path of the K-wire is not straight but slightly curved, i.e. the K-wire deviates from the correct path. Such a deviation may have different reasons, namely (i) the path of the K-wire may not be drilled deeply enough, (ii) a wrong K-wire sleeve may be used, or (iii) a wrong or old K-wire may be used. In the example of FIG. 12 possibilities are shown on the left side to assist a physician in an identification of the possible mistake by providing a list of aspects in form of questions which should be checked by the physician (step S24). Further shown in FIG. 12 is an indication in the x-ray image that the K-wire actually deflects and that there might be a risk when the physician proceeds with the deflected K-wire (step S25).

Furthermore, an overlay of a visualization of a virtual screw and a virtual femur head surface onto the x-ray image may be provided, with the screw arranged in a position which would be achieved when proceeding with the actual (possibly deflected) position of the K-wire as detected in the last image (step S26). Such a visualisation may help a physician to consider the result before actually inserting a bone screw. It may also be considered as to whether the selected screw might be too long so that a proximal end of the screw protrudes out of the bone too far into soft tissue (step S27). The procedural aspect of inserting a K-wire and of checking its position is reflected in steps S23 to S27, i.e. aspect D in FIGS. 1*a* and 1*b*. It will be understood, that all this information, warnings and questions can automatically be omitted in a case in which the K-wire can be detected as being accurately and correct inserted.

Figure 13:
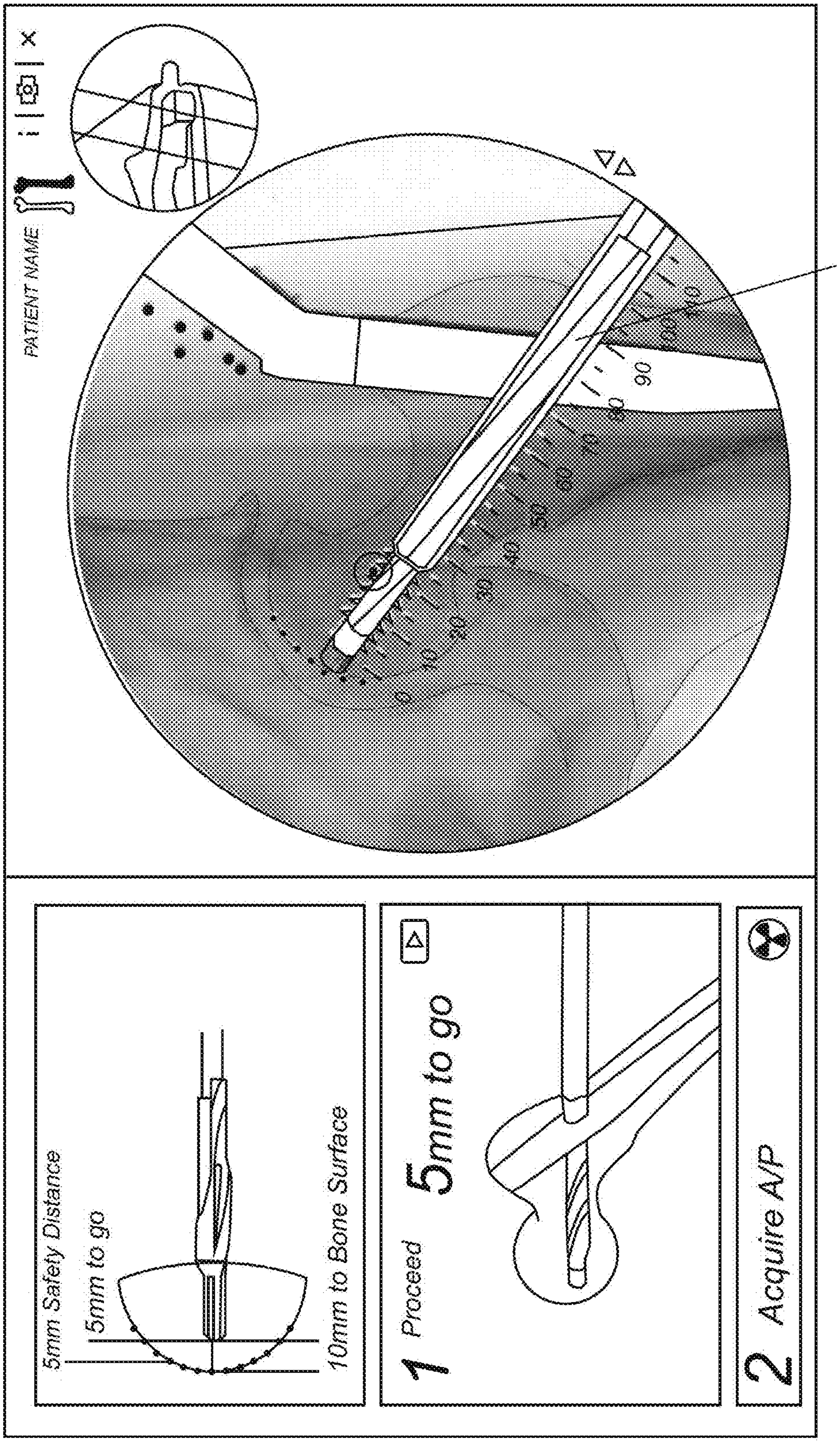
FIG. 13 is an example of a monitor visualization representing a seventh state of progress of the method.

In the example of FIG. 13, the drilling of a bore for receiving the bone screw is addressed. On the right side of the figure, i.e. of a visualization shown on a monitor, an x-ray image is shown of a situation in which the drill 50 has been introduced into the bone. It will be understood that drilling into a bone is critical with respect to the depth. In particular, penetration of a joint surface of the femur head should be avoided to not impair the movability of the hip joint.

To assist a physician in providing an appropriate bore for the bone screw to be implanted, i.e. deep enough but not too deep, outlines of the bone screw together with a scale may be shown in the x-ray image (step S28). Following the same principles as described above, the processing unit detects points related to the reference body, detects outlines of the implant and the drill as well as outlines of the anatomical structure in the vicinity of the implant and drill (step S29), and translates the distances and dimensions into values for instructions (step S31). Here, the system measures the distance between the tip of the drill and the joint surface of the femur head (step S30) and provides the instruction to drill further 5 mm into the bone to achieve an appropriate bore (step S32). Following the drilling, the physician is asked to acquire a further x-ray image so as to control the accurate drilling (step S33). Steps S28 to S33 are grouped together as aspect E of the procedure of FIG. 1*b*.

Figure 14:
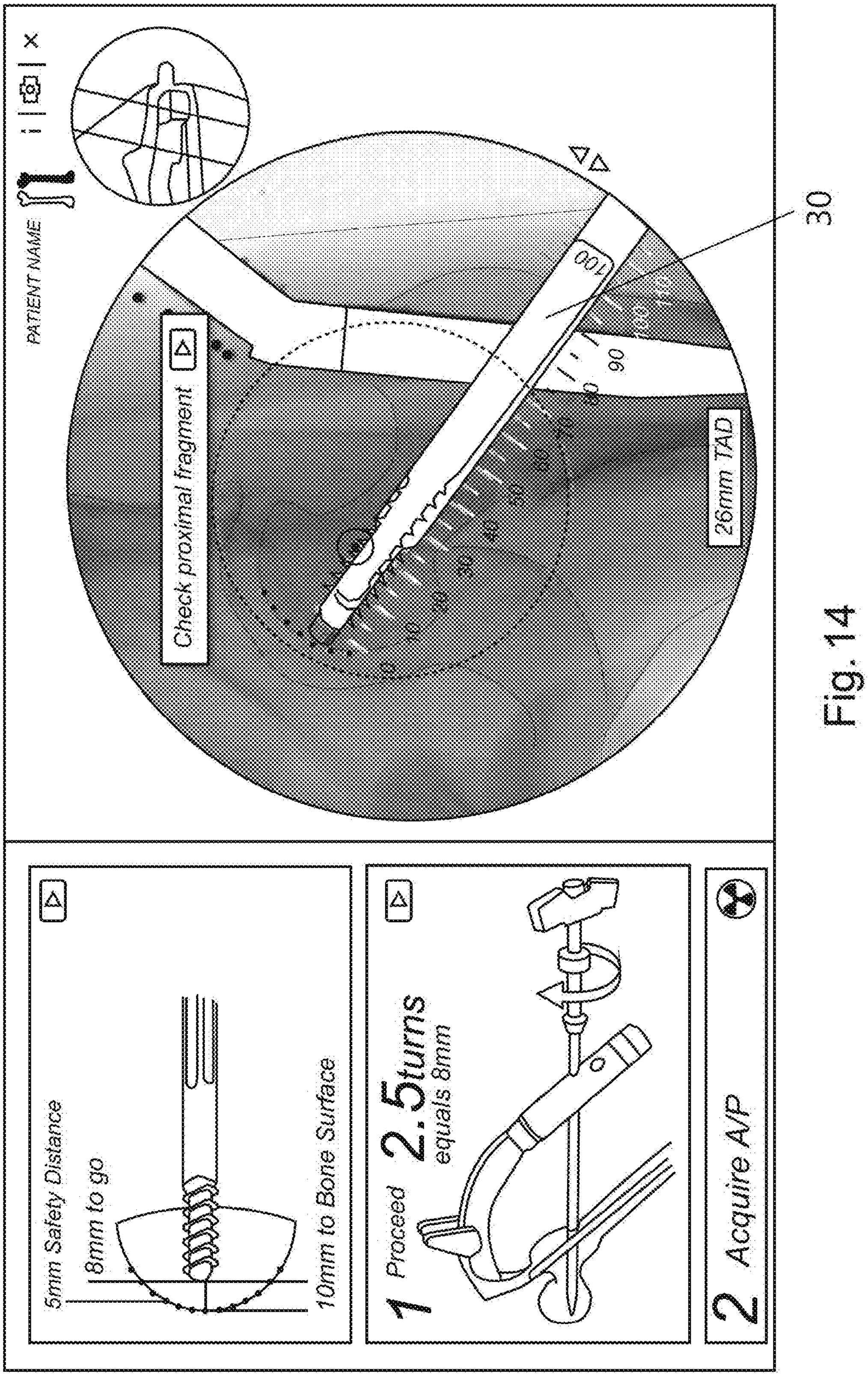
FIG. 14 is an example of a monitor visualization representing a eighth state of progress of the method.
Figure 15:
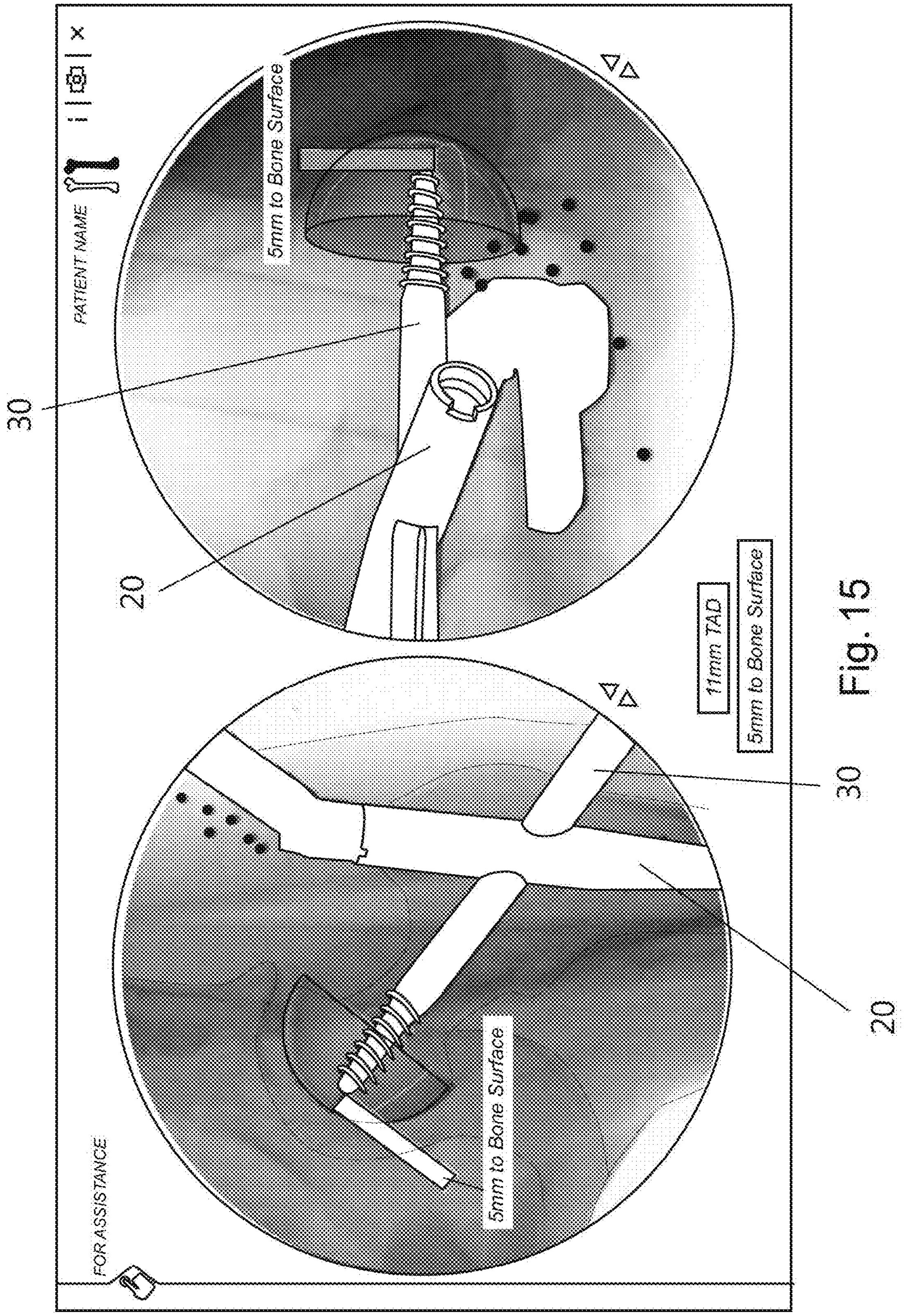
FIG. 15 is an example of a monitor visualization representing a ninth state of progress of the method.

Before introduction of a bone screw 30 into the bone, here a lag screw, the physician may select a screw with a specific length out of a group of possible screw (step S34) and may then start to introduce the selected screw (step S35). Similar to the drilling procedure, the screw will be inserted and before the insertion is completed a control shot is performed to receive a further x-ray image (step S36). Such an image is shown in the example of FIG. 14. Again, the processing unit of the system is configured to extract three-dimensional information out of the projection image (step S37) on the basis of which finally the distance between the tip of the screw and the joint surface of the femur head is measured (step S38). The measured distance can be translated into the instruction to proceed with screwing in of the screw by 2.5 turns (step S39). Thus, the procedure of fixing an intramedullary femur nail by means of a lag-screw includes substantially steps S34 to S39, i.e. aspect F in FIG. 1*b*.

Based on a new image, the correct insertion of the lag screw is verified. Providing an overlay of an appearance of a three-dimensional virtual implant and sub-implant onto the x-ray in both the ML and AP view (step S40), allows for an easier confirmation of the implantation of the implants. The example of FIG. 16 shows such visualization side by side together with information of the distance of the screw tip to the bone surface.

Following the fixation of the intramedullary nail at the proximal end of the femur, a further fixation of that nail at its distal end portion may be desired. In such a case, the system may firstly provide instructions guiding a physician step by step through the procedure (step S41). For example, the instructions may be given (i) to firstly insert a set screw into the proximal end of the nail, (ii) to then attach the distal targeting device at the nail, and also (iii) to shift the c-arm based x-ray imaging device distally so as to be able to image the distal end portion of the nail within the bone.

Comparable to what has been performed at the proximal end of the femur, the procedure at the distal end of the femur start with a detection of points in the first x-ray image which points represent the reference body (step S42), and in a case in which not enough of such points are detectable by the system, the physician is asked to adjust the imaging parameter (step S43).

Figure 16:
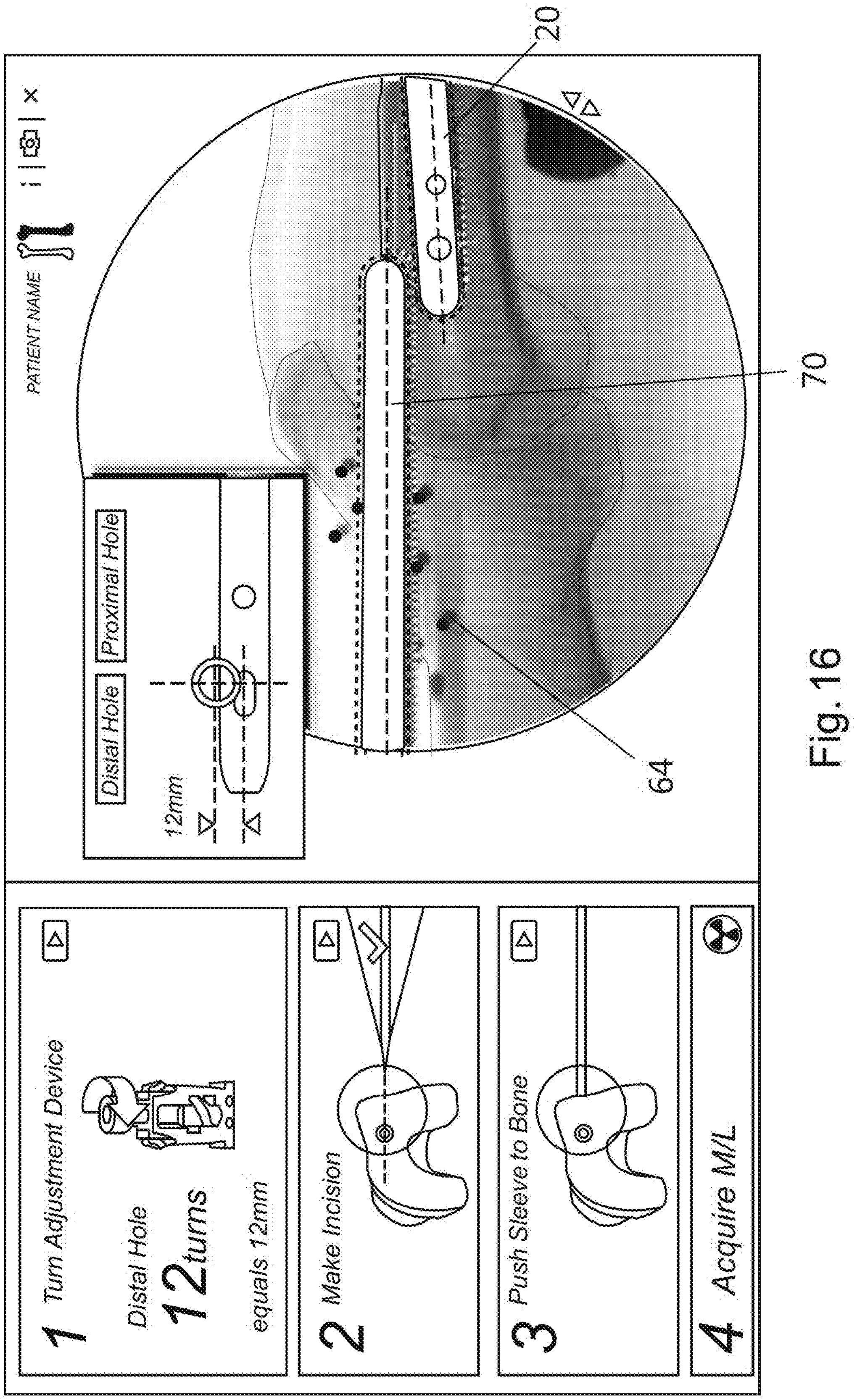
FIG. 16 is an example of a monitor visualization representing a tenth state of progress of the method.

Based on a new image, as shown in the example of FIG. 16, the reference body 64 is detected (step S44), the intramedullary nail 20 as well as a sleeve 70 at the distal targeting device are identified (step S45), and the distance between an axis of the targeting sleeve and a distal locking hole in the nail is measured (step S46). The measured distance is translated into turns for an adjustment screw of the distal targeting device (step S47) and the result of the translation is indicated on the monitor (step S48). After a corresponding adjustment of the targeting device, the physician receives a list of steps which should be performed next. Such steps may be (i) making an incision, (ii) pushing the targeting sleeve to the bone, (iii) generate a control image, (iv) perform drilling, (v) measure the length for the screw to be inserted, and (vi) insert a screw with an appropriate length to fix the distal end of the nail in the bone.

The aspect of distal locking of the intramedullary nail is indicated in FIG. 1*b* as aspect I, i.e. the sequence with steps S44 to S48.

Figure 2:
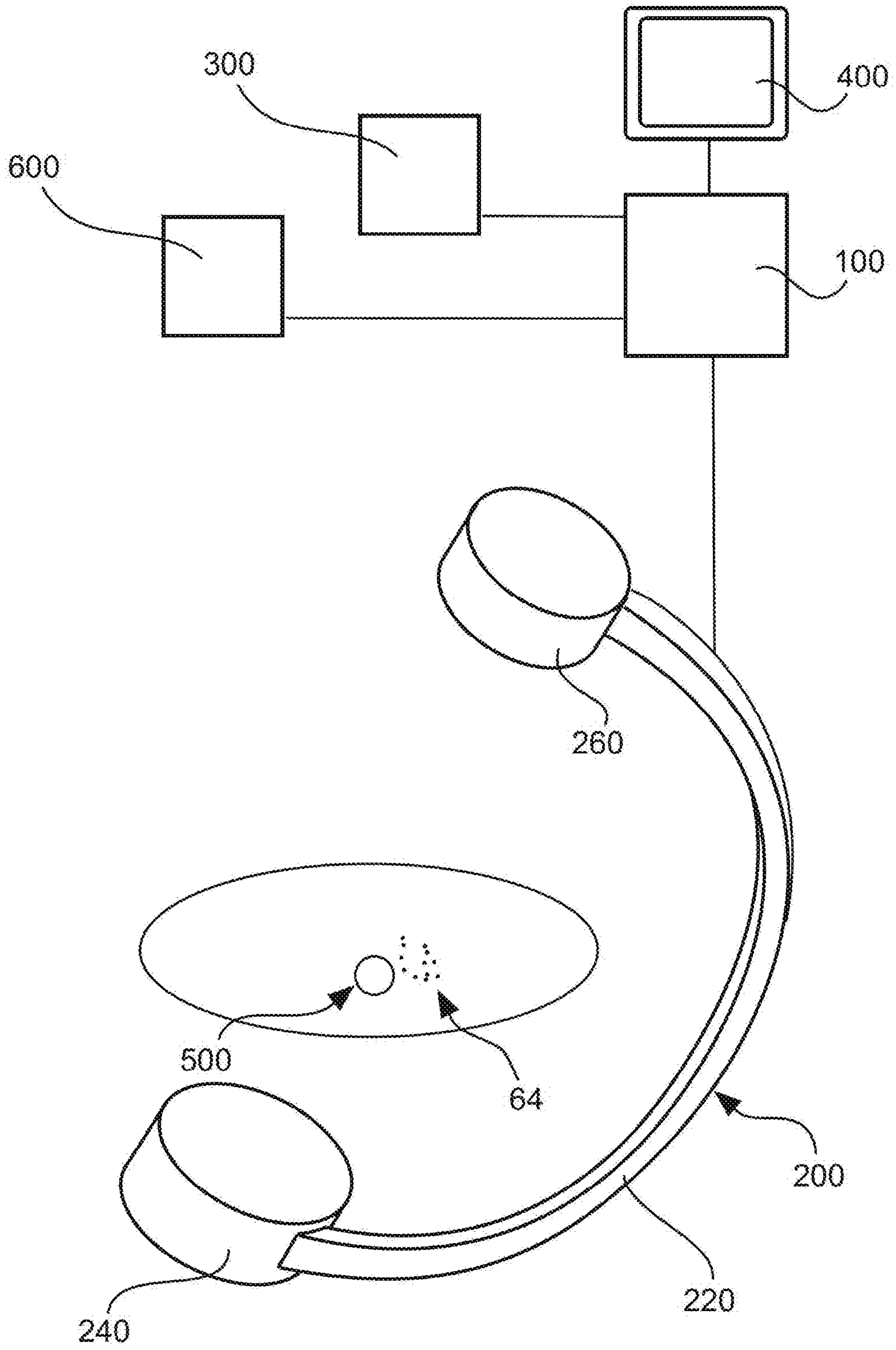
FIG. 2 shows a schematical illustration of a system.

FIG. 2 shows an exemplary embodiment of a device. Substantially, necessary for performing the steps of the method, a processing unit 100 is part of the device.

An exemplary imaging device 200 includes an X-ray source 240, and an X-ray detector 260, wherein these two units are mounted on a C-arm 220.

Furthermore, the system in FIG. 2 includes an input unit 300, by means of which for example an intended imaging direction may be manually entered. Also shown is a connection to a database 600, located for example in a network. The database 600 may comprise information regarding anatomical structures, for example from 3D scans of different anatomical structures, so that the imaged anatomical structure may be compared with this information so as to determine specific anatomical structures. The database may further comprise information regarding a sequence of necessary and/or possible steps of a surgical procedure. It is noted that it is also possible to automatically determine the progress of the surgical procedure based on detectable aspects in an x-ray image, wherein such aspects may be in instrument and/or implant.

Finally, there is an indication in FIG. 2 of an anatomical structure of interest 500 as well as of a reference body 64 formed by a plurality of radiopaque spheres. Within said anatomical structure, for example a bone of a patient may be located which may be subject to the described procedures.

While embodiments has been illustrated and described in detail in the drawings and afore-going description, such illustrations and descriptions are to be considered illustrative or exemplary and not restrictive, the invention is not limited to the disclosed embodiments.

Other variations to the disclosed embodiments can be understood and effected by those skilled in the art in practising the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims.

The mere fact that certain measures are recited and mutually different dependent claims does not indicate that a combination of these measures can not be used to advantage. The computer program may be stored/distributed on a suitable medium such as an optical storage medium or a solid-state medium supplied together with or as a part of another hardware, but may also be distributed in other forms, such as via the Internet or other wired or wireless telecommunication systems. Any reference signs in the claims should not be construed as limiting the scope.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

LIST OF REFERENCE SIGNS

10 femur
12 outer head surface of femur
14 centre of head of femur
20 implant/bone nail
22 implant axis
24 through bore
30 locking screw
32 axis of corridor/screw
40 K-wire
60 aiming device
62 handling device
64 reference body
70 sleeve
100 processing means
200 imaging device
220 C-arm
240 X-ray source
260 X-ray detector
300 input device
400 monitor
500 region of interest
600 database

The invention claimed is:

1. A method of treating a bone fracture comprising:

taking a 2D image of an implant, a reference body, and an anatomical structure with an imaging device;

detecting the reference body in the 2D image, wherein the reference body is in a fixed position relative to the anatomical structure;

detecting a first set of reference points in the 2D image; and determining based only on the 2D image whether the first set of reference points create a medically optimal 3D orientation of the reference body.

2. The method of claim 1, wherein the reference body is in the fixed position adjacent to the anatomical structure.

3. The method of claim 1, wherein the reference body is in the fixed position on the anatomical structure.

4. The method of claim 1, wherein the reference body is in the fixed position inside the anatomical structure.

5. The method of claim 1, further comprising alerting an operator that the medically optimal 3D orientation of the reference body has been created.

6. The method of claim 1, further comprising detecting the bone fracture in the 2D image.

7. The method of claim 1, further comprising positioning the reference body adjacent to the implant.

8. The method of claim 1, further comprising comparing the 2D image with information received from a database.

9. The method of claim 1, further comprising creating a 3D orientation of the reference body based only on the 2D image in that a structure of the reference body allows a determination of the 3D orientation of the reference body based only on the 2D image.

10. The method of claim 9, further comprising determining an actual axis of delivery of a bone screw though an opening extending through the implant.

11. The method of claim 10, further comprising determining an optimal axis of delivery of the bone screw through the opening such that the optimal axis of delivery guides the bone screw toward a medically optimal location.

12. The method of claim 11, further comprising moving the implant such that the optimal axis of delivery and the actual axis of delivery coincide.

13. The method of claim 12, wherein the moving step includes moving the implant such that the optimal axis of delivery extends into a femoral head.

14. The method of claim 9, wherein the creating step includes projecting a first x-ray pattern from the 2D image on a first projection surface to form a pattern of projection points.

15. The method of claim 14, further comprising measuring a distance between a point of the pattern of projection points and another point of the pattern of projection points.

16. The method of claim 15, further comprising comparing the measured distance with a predetermined distance within a database.

* * * * *